(12) United States Patent
Lee et al.

(10) Patent No.: US 7,037,600 B2
(45) Date of Patent: May 2, 2006

(54) RED-EMITTING ORGANIC ELECTROLUMINESCENT ELEMENTS

(75) Inventors: Shuit-Tong Lee, Hong Kong (CN); Chun-Sing Lee, Hong Kong (CN); Liang-Sun Hung, Webster, NY (US); Baoxiu Mi, Hong Kong (CN); Zhi-Qiang Gao, Hong Kong (CN)

(73) Assignee: City University of Hong Kong, Hong Kong (CN)

( * ) Notice: Subject to any disclaimer, the term of this patent is extended or adjusted under 35 U.S.C. 154(b) by 0 days.

(21) Appl. No.: 10/391,265

(22) Filed: Mar. 18, 2003

(65) Prior Publication Data
US 2004/0185298 A1 Sep. 23, 2004

(51) Int. Cl.
*H05B 33/14* (2006.01)
*C09K 11/08* (2006.01)

(52) U.S. Cl. ............... 428/690; 428/917; 252/301.16; 313/504; 313/506

(58) Field of Classification Search ........... 252/301.16; 428/690, 917; 313/504, 506
See application file for complete search history.

(56) References Cited

U.S. PATENT DOCUMENTS 5,935,720 A 8/1999 Chen et al. ............ 428/690
6,720,090 B1 * 4/2004 Young et al. ........... 428/690

OTHER PUBLICATIONS

Mi et al., "New Polycyclic aromatic hydrocarbon dopants for red organic electroluminescent devices", Mar. 18, 2002, Journal Materials Chemistry, vol. 12 (5), pp. 1307-1310.*

(Continued)

*Primary Examiner*—Rena Dye
*Assistant Examiner*—Camie S. Thompson
(74) *Attorney, Agent, or Firm*—Heslin Rothenberg Farley & Mesiti, P.C.

(57) ABSTRACT

Compounds of formula [I]

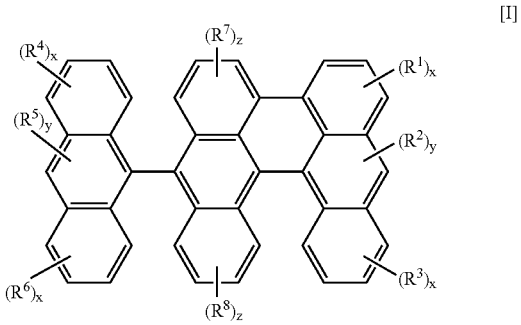

wherein each $R^1$ to $R^8$ is independently selected from the group consisting of halogen atoms, cyano, isocyano, mercapto, amino, carbonyl, carboxy, sulfone, nitro and hydroxy groups, and optionally substituted alkyl, alkenyl, alkynyl, haloalkyl, hydroxyalkyl, aryl, alkoxy, aryloxy, alkylamino, arylamino, alkylarylamino, amide, alkylthio, arylthio, alkoxy carbonyl, siloxy, cyclic hydrocarbon or heterocyclic groups; each x is independently zero, one, two or three; each y is independently zero or one; and each z is independently zero, one, two or three are useful in organic electroluminescence devices. Such compounds are disclosed herein, as well as organic electroluminescence devices using the compounds in the emissive layer.

15 Claims, 3 Drawing Sheets

OTHER PUBLICATIONS

Mueller et al., "Synthesis and Characterization of Soluble Oligo (9, 10-anthrylene)s", Chemische Berichte, (1994) 127, pp. 437-444.*

J.L. Segura, "The Chemistry of Electroluminescent Organic Materials," *Acta Polym.* 49, 319-44 (1998).

C.W. Tang and S.A. Van Slyke, "Organic Electroluminescent Diodes," *Appl. Phys. Lett.*, 51 (12), 913-15 (1987).

C.H. Chen et al., "Recent Developments in Molecular Organic Electroluminescent Materials," *Macromol. Symp.* 125, 1-48 (1997).

U.Mitschke and P. Bäuerle, "The Electroluminescence of Organic Materials," *J. Mater. Chem.* 10, 1471-1507 (2000).

Y. Shirota, "Organic Materials for Electronic and Optoelectronic Devices," *J. Mater. Chem.* 10, 1-25 (2000).

* cited by examiner

RED-EMITTING ORGANIC ELECTROLUMINESCENT ELEMENTS

FIELD OF THE INVENTION

The present invention relates to electroluminescence devices, and more particularly to a novel class of red-emitting luminescent materials for use in such devices.

BACKGROUND OF THE INVENTION

Information displays for instruments, televisions, computers and the like are widely used. In an effort gain display ample, correct, concise, and high-speed information on a machine, the display elements of these information displays have been widely studied.

While cathode ray tubes (CRTs) clearly dominate the market with their bright, saturated colours, they are also known to be heavy, power consuming and bulky. For these reasons, flat panel displays are a highly attractive alternative for computers, television, wall-mounted large-screen video displays and a wide range of other applications.

An example of a flat panel display is an active-matrix liquid-crystal display, these displays being commercially available. Even though this technology is now widely used for laptop computer displays, in general it is not considered to be a widespread replacement for the CRT technology. The major shortcomings of the LCD-based display are that it is an inefficient colour subtractive technology, requiring a power consumptive backlight. Also, it is relatively slow, and has a narrow viewing angle. One alternative to LCDs is based on conventional semiconductor light-emitting diode (LED) technology. However, very high costs associated with the requirement of epitaxial multilayer structures make them an unlikely choice for use in low-cost displays in the near future.

A promising flat panel display free from the above-mentioned disadvantages is based on organic light-emitting diodes (OLEDs) which use an organic luminescent material for light emission. The organic luminescent materials are very attractive due to their versatility, richness in blue photoluminescence, and high photo-luminescent quantum yields.

Further advantages of the OLED display are that they are self-luminous, light weight, capable of high-speed response, and independent of viewing angle. It is expected that these advantages will be successfully exploited, and that a commercial use for organic EL devices will be realised in the near future.

To obtain high-performance OLEDs with low carrier injection barriers, high electroluminescence (EL) efficiency and long lifetime, materials design and device configurations are two important factors. It is desirable that the OLED materials possess the following properties: good carrier transport properties, high photoluminescence (PL) quantum yield, and suitable ionisation potential (IP) and/or electron affinity (EA). The synthesis of highly fluorescent and stable materials that can be utilised in OLEDs is one of the most challenging works in this field.

Many materials are known which emit green or blue light. However, few satisfactory red-emitting materials are known.

Some organic compounds with red emission have been reported, such as pyran-containing compounds, porphyrin compounds and europium metal complexes. Due to the instability of rare earth metal complexes during thermal deposition, no europium metal complexes show a practical operation lifetime, even though they have a sharp emission peak with high colour purity. A known red dopant from the porphyrin group of compounds is platinum octaethylporphyrin (PtOEP), however devices using this compound doped in $AlQ_3$ do not have brightness or chromaticity which is acceptable for practical applications. Pyran-containing compounds include 4-dicyanomethylene-2-methyl-6-(p-dimethylaminostyryl)-4H-pyran (DCM), 4-(dicyanomethylene)-2-methyl-6-(1,1,7,7-tetramethyljulolidin-9-yl)-4H-pyran (DCJT) and 4-(dicyanomethylene-2-tert-butyl-6-(1,1,7,7-tetramethyljulolidin-9-yl)-4H-pyran (DCJTB). A disadvantage of these compounds is that they have a highly concentration-dependent emission. A desirable red colour can only be obtained at high concentration, which dramatically reduces luminance efficiencies.

Thus, despite significant developments in the field of OLEDs, red emission from OLEDs with high colour purity and good stability is still needed.

Polycyclic aromatic hydrocarbons (PAHs) have very high PL quantum yield and have already been used in OLEDs. The pure hydrocarbon conjugated structure of the compounds intrinsically determines their relatively high carrier transport abilities. Most PAHs are highly luminescent and relatively stable. Examples using this kind of material in OLEDs include T. Sano et al, *Syn. Met.*, 91, 27 (1997), and U.S. Pat. Nos. 5,935,721 and 5,858,564.

It is known that the energy gap of PAH compounds depends on the conjugation length in the molecules, with a longer conjugation length resulting in a smaller HOMO-LUMO energy gap. Materials with red emission generally have a narrow energy gap. However, many known PAHs emit only in the blue and yellow regions, with only a few PAH compounds reported to have emission about 600 nm. Moreover, PAH compounds with more fused carbon rings, and hence a longer conjugation length, have a high sublimation temperature, which limits the application of red-emission PAH compounds in OLEDs.

SUMMARY OF THE INVENTION

The object of the present invention is to provide further PAH compounds which generate red emission and can be used in OLED fabrication.

In our invention, we have synthesised a new PAH compound, 1,9-peri-(9'-anthrylene)-10-(9'-anthryl)anthracene (pAAA), and a number of its derivatives, and have utilised these compounds in OLED fabrication.

According to present invention there is provided a compound of formula [I]:

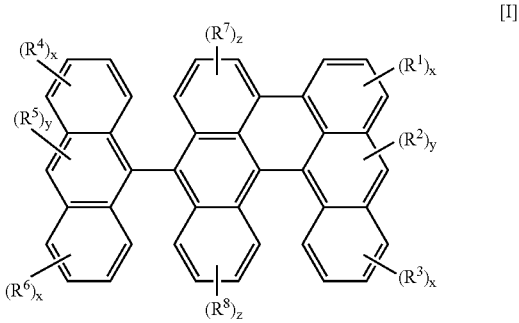

wherein each $R^1$ to $R^8$ is independently selected from the group consisting of halogen atoms, cyano, isocyano, mercapto, amino, carbonyl, carboxy, sulfone, nitro and hydroxy groups, and optionally substituted alkyl, alkenyl, alkynyl, haloalkyl, hydroxyalkyl, aryl, alkoxy, aryloxy, alkylamino, arylamino, alkylarylamino, amide, alkylthio, arylthio, alkoxy carbonyl, siloxy, cyclic hydrocarbon or heterocyclic groups, each x is independently selected from zero, one, two and three, each y is independently selected from zero and one, and each z is independently selected from zero, one, two and three.

When each x is zero, each y is zero and each z is zero, then the compound is called pAAA. When at least one x, y and z is not zero, then the compound is known as a pAAA derivative.

According to a further embodiment, there is provided an organic electroluminescence device comprising an anode, a cathode, a luminescent layer, at least one hole-transporting layer disposed between the said anode and said luminescent layer, at least one electron-transporting layer disposed between said cathode and said luminescent layer, and a substrate present on either the anode or cathode, wherein the luminescent layer comprises a compound of formula [I], as defined above.

The invention also provides a method of using a compound of formula [I], as defined above, in an organic electroluminescence device, wherein the method comprises providing a compound of formula [I], and incorporating the compound as a luminescent material within an electroluminescence device which further comprises an anode, a cathode, a hole-transporting layer and an electron-transporting layer.

There is also provided a self-luminous display incorporating an electroluminescence device as defined above, which uses a compound of formula [I] as the luminescent material.

The compounds of the invention have a number of advantages, such as being highly efficient with a narrow emission peak and a stable conjugated system. OLEDs including these compounds exhibit high power efficiency, colour purity and stability.

DETAILED DESCRIPTION OF THE INVENTION

Figure 1:
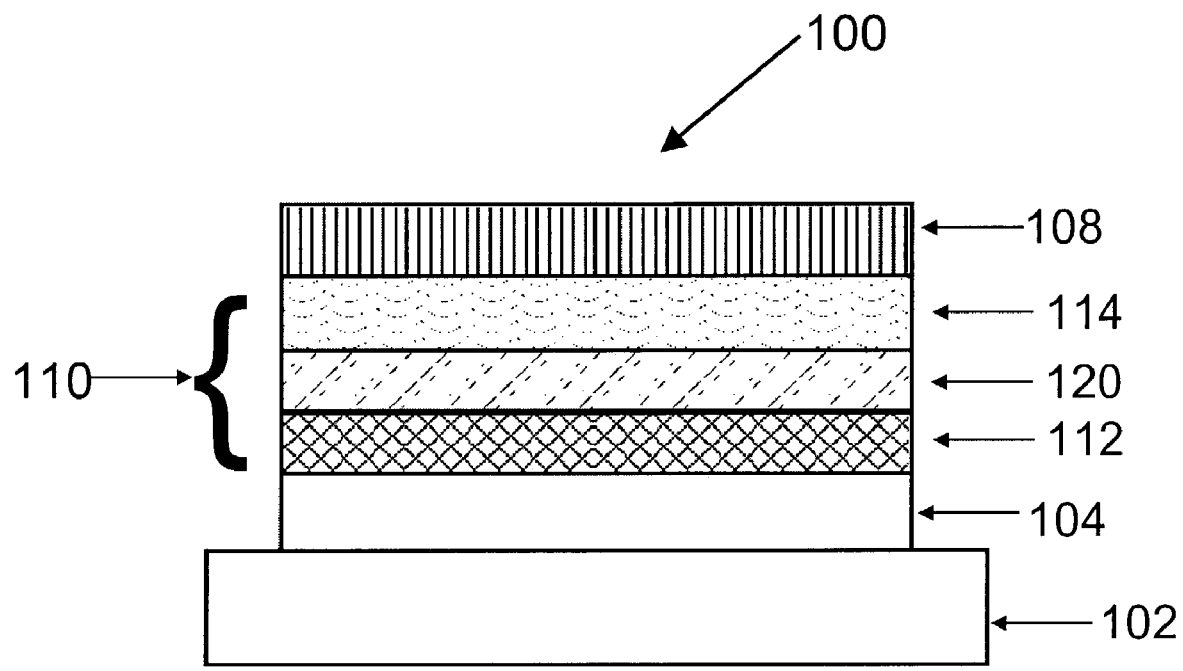
FIG. 1 is a schematic diagram of an embodiment of organic LEDs in accordance with the present invention.

Unless otherwise stated in the following description, the term alkyl represents an alkyl group containing from 1 to 18, preferably 1 to 10, and more preferably 1 to 6, carbon atoms. Particularly preferred alkyl groups include methyl, ethyl, propyl, butyl, sec-butyl, tert-butyl, pentyl, hexyl, heptyl, octyl and stearyl.

The terms alkenyl and alkynyl represent alkenyl and alkynyl groups respectively having from 2 to 18, preferably from 2 to 10, and more preferably from 2 to 6 carbon atoms. One of the preferred alkenyl groups is an allyl group, of formula —$CH_2CH=CH_2$.

The term halogen represents a chlorine, fluorine, bromine or iodine atom, with chlorine and fluorine being preferred. A group containing a halogen atom, e.g. haloalkyl, may contain one or more of these halogen atoms.

Cyano represents a group of formula —CN, and isocyano a group of formula —NC. Nitro represents an —$NO_2$ group.

Haloalkyl represents any alkyl group substituted by one or more halogen atoms. Preferably haloalkyl represents trichloromethyl or trifluoromethyl.

Hydroxy represents an —OH group, and hydroxyalkyl represents an alkyl group substituted with at least one hydroxy group. The alkyl group preferably has from 1 to 4 carbon atoms.

Aryl represents a cyclic hydrocarbon having at least one aromatic ring, and having from 5 to 30, preferably from 6 to 14, carbon atoms. Aryl preferably represents a group selected from the group consisting of phenyl, naphthyl, anthryl, biphenyl, triphenyl, tetraphenyl, o-tolyl, m-tolyl, p-tolyl, o-xylyl, m-xylyl, p-xylyl, or o-cumenyl, m-cumenyl, p-cumenyl and styryl. Phenyl and naphthyl groups are particularly preferred.

The term alkoxy represents an alkyl group linked via an oxygen atom. Preferably alkoxy represents methoxy, ethoxy, propoxy, butoxy, sec-butoxy, tert-butoxy or stearyloxy. Similarly, the terms alkenyloxy and aryloxy represent alkenyl and aryl groups respectively linked via an oxygen atom. Preferably aryloxy represents phenoxy.

Amino represents a group of formula —$NH_2$. Alkylamino represents any amino group of formula —NHR' or —NRR' where R and R' are optionally substituted alkyl groups, preferably having from 1 to 10, more preferably from 1 to 4, carbon atoms. Preferred alkylamino groups are methyl amino (i.e. —NHMe), ethyl amino, propyl amino, butyl amino, sec-butyl amino, tert-butyl amino, pentyl amino, hexyl amino, heptyl amino, octyl amino, stearyl amino, dimethyl amino (i.e. —$NMe_2$), diethyl amino, dipropyl amino, dibutyl amino, disec-butyl amino, ditert-butyl amino, dipentyl amino, dihexyl amino, diheptyl amino, dioctyl amino and distearyl amino.

Arylamino represents any amino group of formula —NHR" or —NHR"R'" where R is an optionally substituted aryl group as defined above. The aryl group is preferably selected from the group consisting of phenyl and naphthyl, anthryl and tolyl. Preferred arylamino groups include phenylamino, diphenylamino and phenylnaphthylamino.

Amide represent a group of formula —NRC(O)R, wherein R is a hydrogen atom or an optionally substituted alkyl group, preferably an alkyl group having from 1 to 4 carbon atoms.

The term alkoxy carbonyl represents an alkoxy group as defined above linked via a carbonyl group. Preferably the alkyl group of the alkoxy group has from 1 to 6, more preferably from 1 to 4, carbon atoms. The term carboxy represents a group of formula —COOH.

Mercapto represents the group —SH. Alkylthio represents an optionally substituted alkyl group linked by a sulphur atom. Preferred alkylthio groups include methylthio, ethylthio, propylthio, butylthio, sec-butylthio and tert-butylthio. Similarly, arylthio represents an optionally substituted aryl group linked by a sulphur atom. Preferably arylthio represents phenylthio.

Siloxy represents a group of general formula —$OSiR_3$, where each R group is independently selected from the group consisting of a hydrogen atom and an optionally substituted alkyl group. The alkyl group preferably has from 1 to 6, more preferably 1 to 4, carbon atoms.

Cyclic hydrocarbon represents both mono- and polycyclic hydrocarbons, which may be saturated or unsaturated, having from 3 to 20, more preferably from 3 to 10, carbon atoms. Preferred cyclic hydrocarbons include cyclohexyl, cyclopentyl, cycloheptyl and cyclooctyl.

The term heterocyclic represents groups having between 3 and 20, more preferably between 3 and 10, carbon atoms and having one or more 4, 5, 6 or 7 member saturated or unsaturated rings containing 1, 2 or 3 oxygen, nitrogen or sulphur atoms. When the heterocyclic group comprises one or more aromatic rings, it is known as a heteroaryl group. Representative heterocyclic groups include pyranthrenyl, oparenyl, thienyl, furyl, pyrrolyl, pyrrolidinyl, imidazolyl, piperazinyl, piperidinyl, pyrazolyl, pyridyl, pylazinyl, pyrimidinyl, pyridazinyl, indolyl, quinolyl, isoquinolyl, phthalazinyl, quinoxalynyl, quinazolynyl, carbazolyl, acrydinyl, phenadinyl, furluryl, isochiazolyl, isothiazolyl, isoquixazolyl, furazanyl, phenoquisadinyl, benzthiazolyl, benzoxazlyl and benzoimidazolyl. Particularly preferred heterocyclic groups include 5- or 6-membered rings containing 1 or 2 oxygen, nitrogen or sulphur atoms.

Carbonyl (or acyl) represents a group having the general formula —C(O)R, where R is a hydrogen atom or an optionally substituted alkyl group. The alkyl group preferably has from 1 to 6, more preferably 1 to 4, carbon atoms.

Sulfone (or alkylsulphonyl) represents a group having the general formula —$SO_2R$, where R is a hydrogen atom or an optionally substituted alkyl group. The alkyl group preferably has from 1 to 6, more preferably 1 to 4, carbon atoms.

When any of the groups listed above are described as optionally substituted, the substituent groups include halogen atoms, hydroxy, cyano, amino, nitro, alkyl, cyclic hydrocarbon, haloalkyl, alkoxy, haloalkoxy, carboxy, alkylthio, alkylamino, arylamino, alkoxy carbonyl, siloxy, aryl, aryloxy, alkenyl, alkenyloxy and alkynyl, as well as cyclic hydrocarbon and heterocyclic groups. Preferred optional substituents include alkyl, haloalkyl, aryl, alkoxy, aryloxy, alkylamino, arylamino, alkylthio, arylthio, alkoxy carbonyl, siloxy, cyclic hydrocarbon and heterocyclic groups, with alkyl groups being particularly preferred.

The components of the electroluminescence device of the present invention will now be described individually in more detail, and with reference to FIG. 1. FIG. 1 depicts an organic EL device 100 according to the present invention. The device comprises, in order, a transparent substrate 102, a bottom electrode layer 104 (anode), an organic layer structure 110, and a top electrode layer 108 (cathode). The organic layer structure 110 in FIG. 1 comprises a hole transport layer (HTL) 112, an emissive, or luminescent, layer (EL) 120, and an electron transport layer (ETL) 114.

Substrate

The substrate 102 is used as a support for the organic electroluminescence device 100 of the present invention, and can be made from an optically transparent material or an opaque material. It preferably consists of a quartz or glass sheet, a metal sheet or foil, or a plastic film or sheet. The most preferred materials are a transparent glass sheet or transparent synthetic resin such as polyester, polycarbonate, and polysulfone. However, an opaque substrate can also be used, and may be a ceramic material or a semiconductor. The substrate can be in contact with the bottom electrode layer 104 (as shown in FIG. 1), or alternatively can be in contact with the top electrode layer 108.

Top and Bottom Electrode Layers

The bottom electrode 104, or anode, is a conductive layer, preferably having a high-work function greater than 4.1 eV. It may be either transparent or opaque. Suitable materials are selected from metal oxides, gallium nitride, zinc selenide and zinc sulphide. The metal oxides are preferably selected from indium tin oxide (ITO), tin oxide, magnesium indium oxide, fluorine tin oxide, nickel tungsten oxide, cadmium tin oxide, indium zinc oxide and aluminium zinc oxide. When the substrate 102 is opaque and formed of a ceramic material or a semiconductor, the bottom electrode 104 is preferably selected from a metal or metal alloy having a work-function greater than 4.1 eV. Suitable metals include gold, iridium, palladium and platinum. This layer may be deposited by sputtering, laser ablating and other known surface coating techniques.

The top electrode layer 108, or cathode, is a metal or metal alloy electrode, preferably having a work function less than 4 eV. Suitable materials include Mg:Ag, Li:Al, Mg:In, which act as an electron injectors. This layer is preferably about 50–300 nm thick, and may be deposited by thermal evaporation.

Hole Transport Layer (HTL)

A hole transport layer (HTL) 112 is located on the bottom electrode, and comprises a compound which is able to transport holes efficiently from the bottom electrode to the luminescent layer between the electrodes to which an electric field is applied.

Suitable materials for the HTL include hole-transporting aromatic tertiary amine molecules. Representative examples are the diamine derivatives shown below:

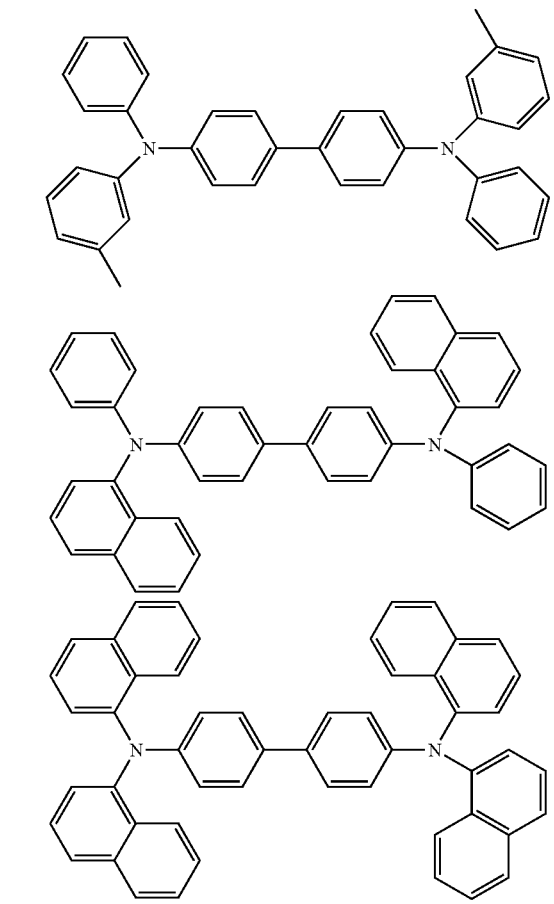

-continued

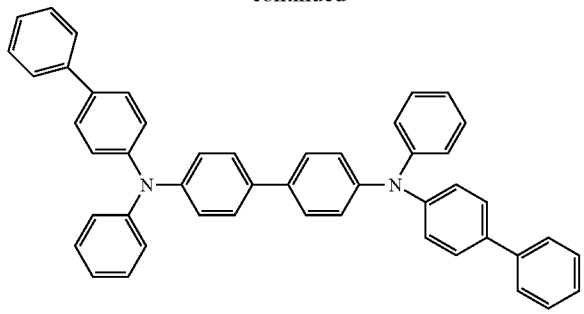

The HTL is preferably present in a thickness of from 30–200 nm. Other compounds which can be used for the HTL include carbazole derivatives and starburst amine derivatives such as 4,4',4''-tris(3-methylphenyl phenylamino)triphenylamine.

The materials mentioned above are applied to the bottom electrode layer by any conventional method, but are preferably applied by thermal evaporation under vacuum conditions.

Electron Transport Layer (ETL)

The electron transport layer (ETL) 114 comprises an electron-transporting material which is such that electrons can be injected from the top electrode layer easily and such that the mobility of transporting electrons is excellent. The ETL is preferably formed from a benzazole compound, or a metal chelated oxinoid compound. An example of such a metal chelated oxinoid compound is:

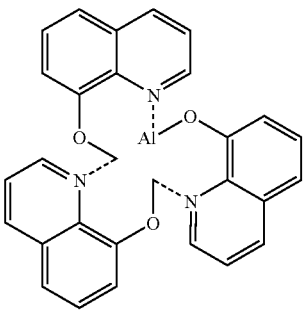

The ETL is preferably from 30–150 nm in thickness. Other compounds which can be efficiently used in the ETL include 1,3,4-oxadiazole derivatives and 1,2,4-triazole derivatives. The ETL may be applied by any conventional method, but thermal evaporation under vacuum is preferred. Moreover, a good capability of forming a thin film is also desirable.

Emissive Layer (EL)

The emissive layer 120 comprises a luminescent material according to formula [I] as defined above. The electrons and holes recombine in the emissive layer and cause luminescence.

The emissive layer may be formed from a compound of formula [I] alone or, more preferably, by doping a compound of formula [I] within a host material. Suitable host materials include the materials which are used as the ETL or the HTL, described above. For example, suitable host materials include tris(8-hydroxy-quinolinato)aluminium (AlQ$_3$), N,N'-bis(1-naphthyl)-N,N'-diphenyl-1,1'-biphenyl-4,4'-di-amine (NPB) and a trimer of N-arylbenzimidazoles (TPBI). Particularly good results were achieved with AlQ$_3$. The dopant is preferably present within the host material at a level of from 0.5 to 2% by weight.

Other luminescent compounds may also be included within the emissive layer, if desired. For example, emitting assistants such as rubrene or 7-naphthylbenzo[α] perylene can be used to facilitate energy transfer from the host material to the dopant.

In formula [I] where at least one of x, y and z is not zero it is preferred that each $R^1$ to $R^8$ is independently selected from the group consisting of hydrogen and halogen atoms, hydroxy, cyano, isocyano, amino, carbonyl, carboxy, sulfone and nitro groups, and optionally substituted alkyl, alkenyl, allyl, alkoxy, aryl, alkylamino, arylamino, amide, alkoxy carbonyl and heterocyclic groups. Where more than one substituent is present on the same phenyl ring (e.g. where x or z is two or three), these substituents need not represent the same group.

Some particularly preferred substituents include alkyl groups having from 1 to 4 carbon atoms, such as methyl, ethyl, propyl, iso-propyl, butyl, sec-butyl and tert-butyl; alkenyl groups having from 1 to 4 carbon atoms and at least one carbon-carbon double bond, such as —CH=CHCH$_2$ and —CH$_2$CH=CH$_2$; alkylamino or arylamino groups wherein the alkyl groups have from 1 to 4 carbon atoms, such as methyl or ethyl, or wherein the aryl groups have one or two aromatic rings, such as phenyl or naphthyl; and also heterocyclic rings, such as saturated or unsaturated 5- or 6-membered rings containing one or more nitrogen, oxygen or sulphur atoms.

The phenyl rings bearing the $R^1$ to $R^8$ groups may be substituted at any available position. The value of each x may be from zero to three, thus the phenyl rings bearing the $R^1$, $R^3$, $R^4$, $R^6$ groups can have from zero to three of these substituents. It is preferred that x is either zero or one, with zero being preferred. The value of each y may be either zero or one, although zero is preferred. The value of each z may be from zero to three, although it is preferred that each z is zero.

When at least one x, y or z is not zero, the substituents may be present in any substitution pattern. Preferred compounds include those where $R^1$ is the same as $R^4$, $R^2$ is the same as $R^5$, or $R^3$ is the same as $R^6$, in particular where $R^1$ to $R^3$ are identical to $R^4$ to $R^6$ respectively. In some embodiments, $R^1$, $R^3$, $R^4$ and $R^6$ may be the same; $R^1$, $R^2$, $R^4$ and $R^5$ may be the same; or $R^2$, $R^3$, $R^5$ and $R^6$ may represent the same group. Thus, it may be preferred that, when substituents are present, they are arranged symmetrically about the vertical axis of the central anthryl group.

In a particularly preferred embodiment, each x, y and z is zero, and the compound is pAAA:

pAAA

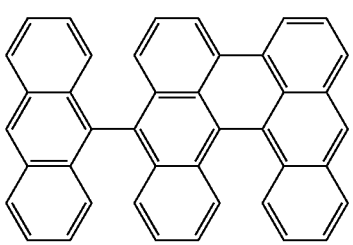

Other preferred compounds of formula [I] include:
(a)
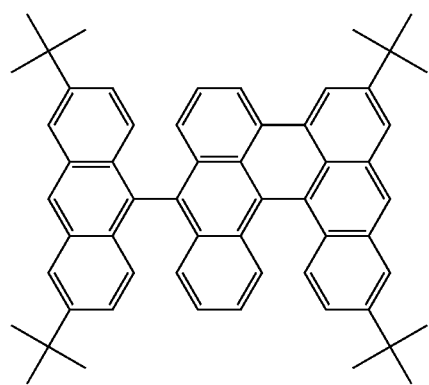
(b)
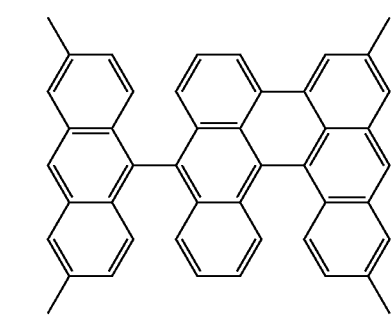
(c)
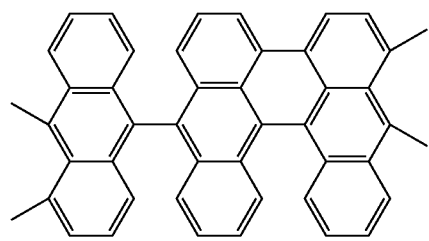
(d)
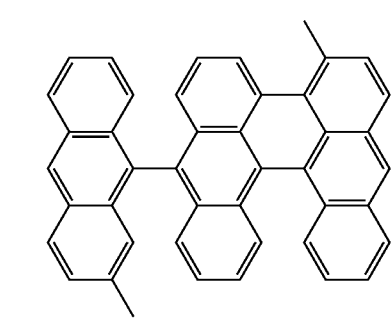
(e)
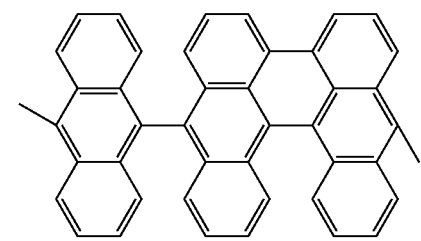
-continued
(f)
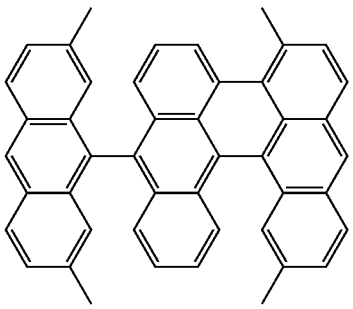
(g)
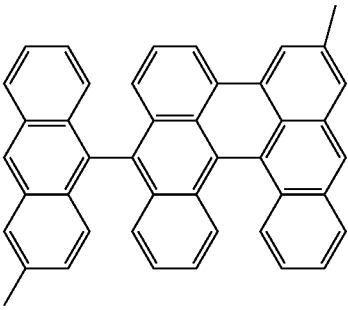
(h)
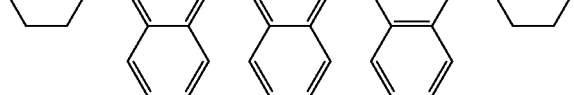
(i)
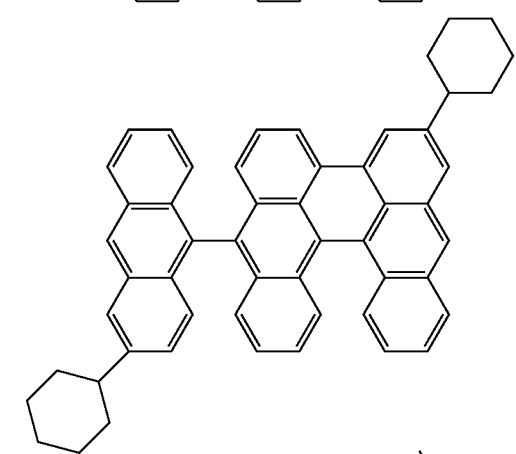
(j)
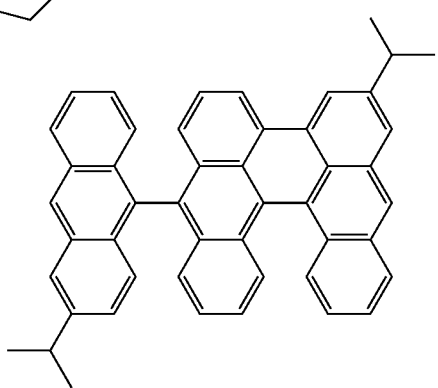

-continued
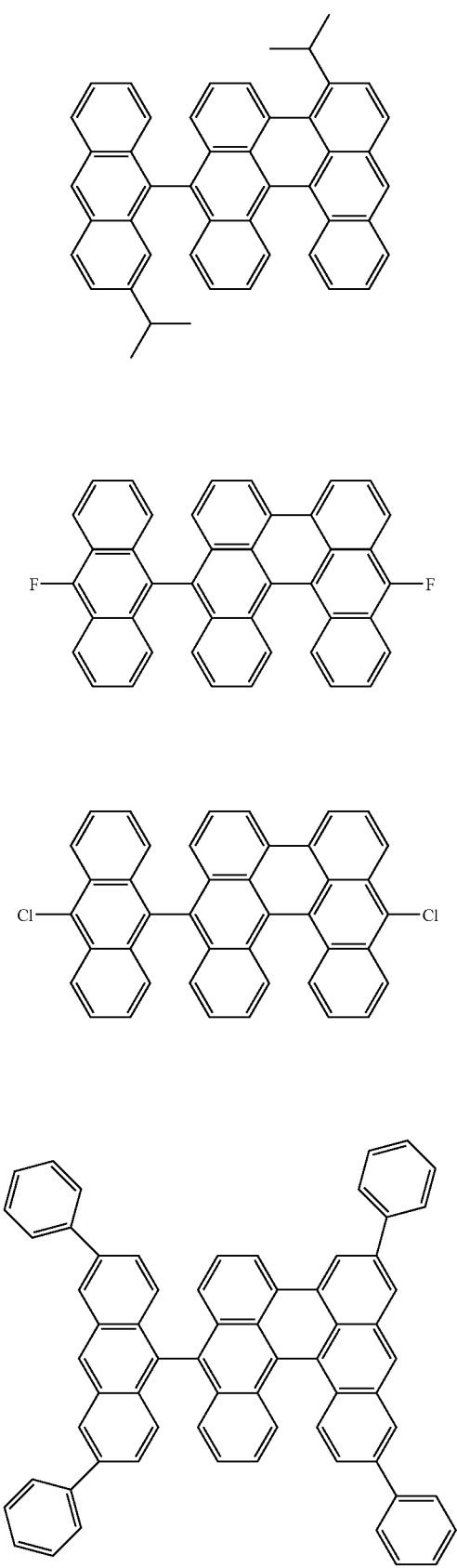
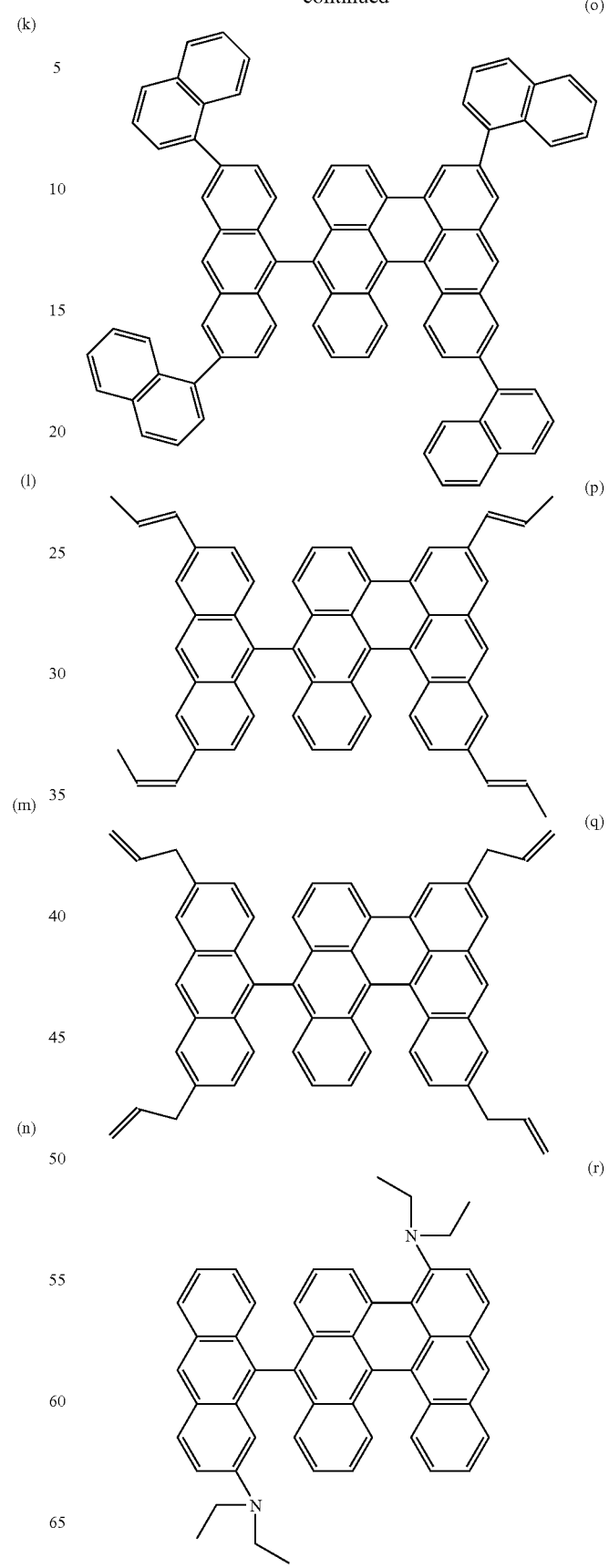

-continued

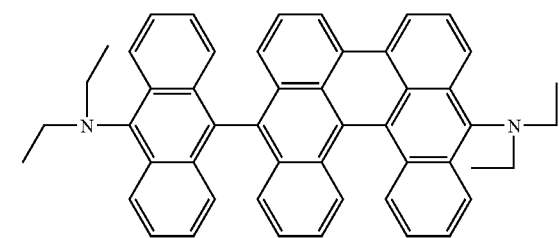
(s)

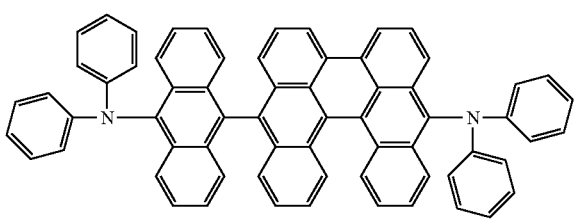
(t)

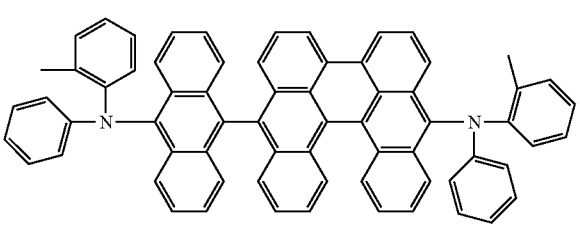
(u)

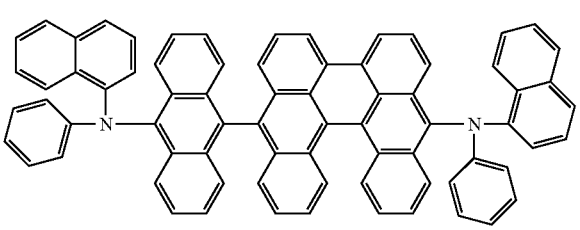
(v)

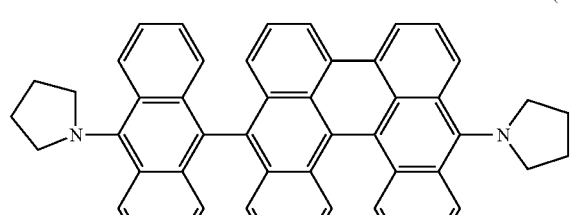
(w)

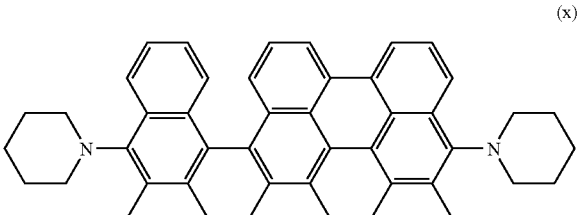
(x)

In the examples above, compounds (a) to (k) are alkyl derivatives of pAAA, while compounds (I) and (m) are halogen derivatives. Compounds (n) and (O) are representative aryl derivatives, and compounds (p) and (q) are alkenyl and allyl derivatives respectively. Compounds (r) to (x) belong to the group of tertiary amino derivatives of pAAA.

The pAAA and pAAA derivatives of the invention can be synthesised by a three step reaction described hereafter. The first step is via a lithium reaction reported by J. D. Buhler, *J. Org. Chem.*, 38, 904 (1973):

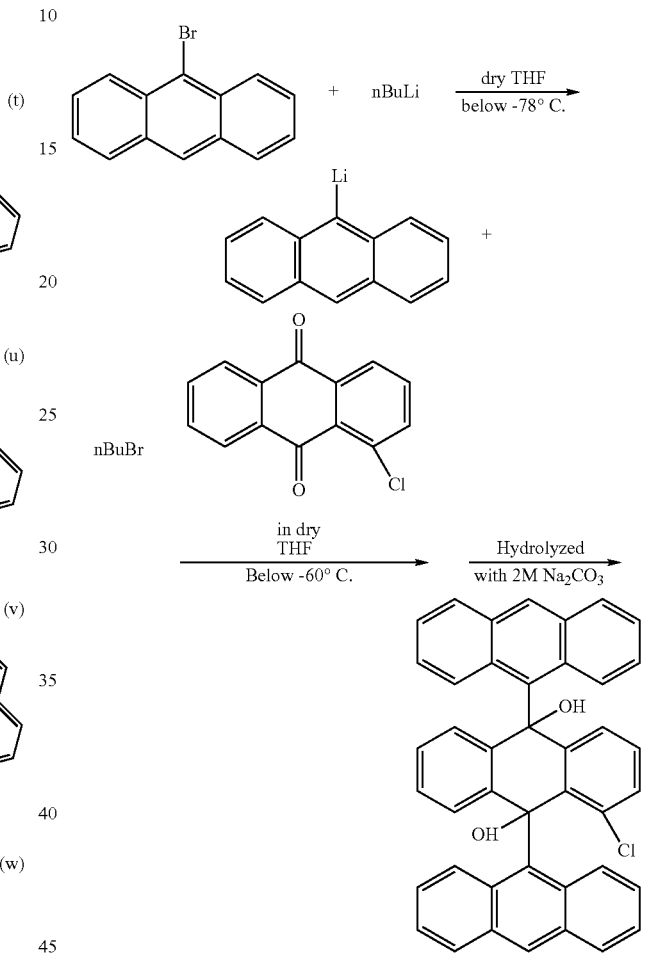

The second and third steps are via a method reported by E. Clar et al, *J. Chem. Soc.*, 1108 (1954):

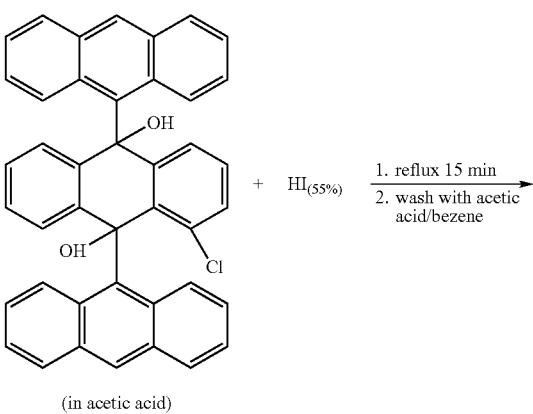

(in acetic acid)

-continued

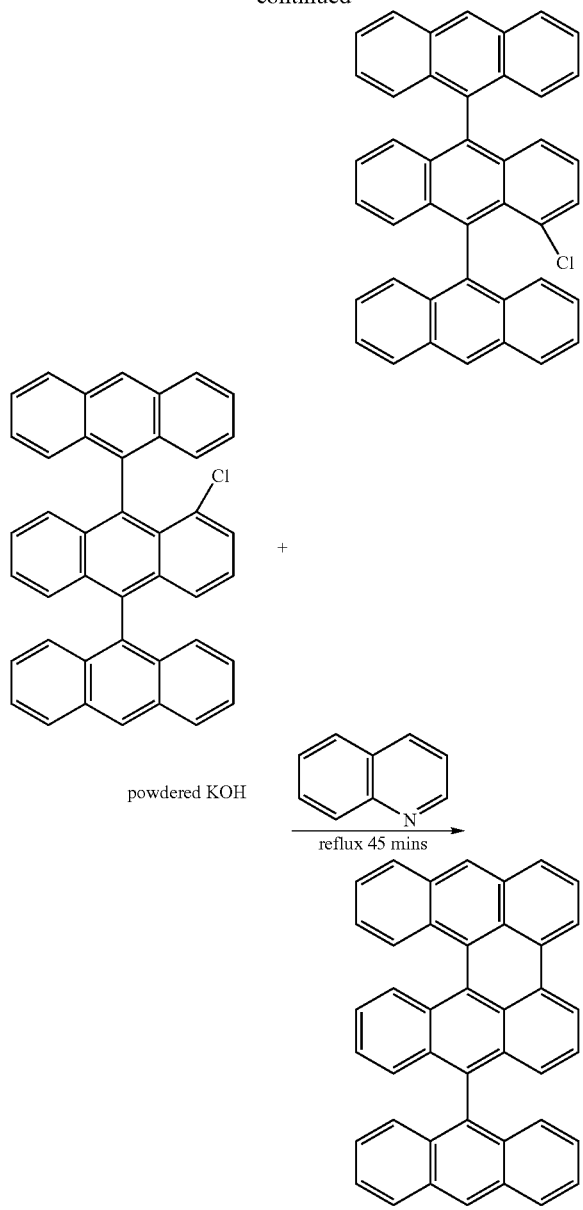

While this synthetic scheme has been illustrated with the synthesis of pAAA, it can readily be modified in order to produce derivatives of pAAA, wherein the various phenyl rings are substituted with $R^1$ to $R^6$.

Other Materials

Other variations and modifications of the devices described above will be apparent to the skilled person.

The organic electroluminescence devices of the present application have a wide variety of applications, for example in monochrome and multi-colour displays. In particular, they can be used in self-luminous displays. They can also be used as a light source, or for many other optical applications.

EXAMPLES

The present invention will be explained in more detail with reference to the Examples which follow.

Example 1

Synthesis of 1-chloro-9,10-dihydro-9,10-di-9,10-anthrylanthracene-9,10-diol using lithium reagent In a 100 ml flask, 3.2 g (12.4 mmol) 9-bromoanthracene (FW: 257.14) and 8 ml dry THF were introduced. The temperature was lowered to −78° C. 8.9 ml (14.2 mmol) of 1.6 M n-BuLi hexane solution was added dropwise via an addition funnel. The dark orange suspension was obtained and stirred at this temperature for half an hour. Then 1.5 g (6.2 mmol) 1-chloro-9,10-anthroquinone (FW: 242.66) in 30 ml dry THF was added via additional funnel. The reaction mixture was allowed to warm up to room temperature at constant stirring for 1 hour, and was then hydrolysed with 30 ml 2 M $Na_2CO_3$ under $N_2$ for another hour. The organic layer was separated and the water layer was extracted with THF three times. The solvent was removed and the organic layers were collected, combined the first separated organic layer, and washed with ether to obtain a pale yellow product, 1-chloro-9,10-dihydro-9,10-di-9'-anthrylanthracene-9,10-diol.

Example 2

Synthesis of 1-chloro-9,10-di-9'-anthrylanthracene

A suspension of 2.5 g (4.2 mmol) of 1-chloro-9,10-dihydro-9,10-di-9'-anthrylanthracene-9,10-diol (FW: 599.15) in 42 ml acetic acid and 2.3 ml (16.8 mmol) hydriodic acid (55%, d=1.70, FW: 127!91) was heated under reflux for 15 min, cooled, filtered, and washed with acetic acid and benzene, to give a yellow product, which was crystallised from 1,2,4-trichlorobenzene to get pure product.

Example 3

Synthesis of 1,9-peri-(9'-anthrylene)-10-(9'-anthryl)anthracene (pAAA)

A mixture of 2 g (3.5 mmol) 1-chloro-9,10-di-9'-anthrylanthracene (FW:565.1), 10 g (178 mmol) powdered potassium hydroxide (FW: 56.11), and 12 ml quinoline was heated under reflux for 45 min. The reaction colour changed through red to purple. The quinoline layer was decanted into dilute hydrochloric acid, to obtain a dark purple precipitate. After washing with hydrochloric acid and water, and drying, a column was used to obtain a purple-coloured product.

Figure 2:
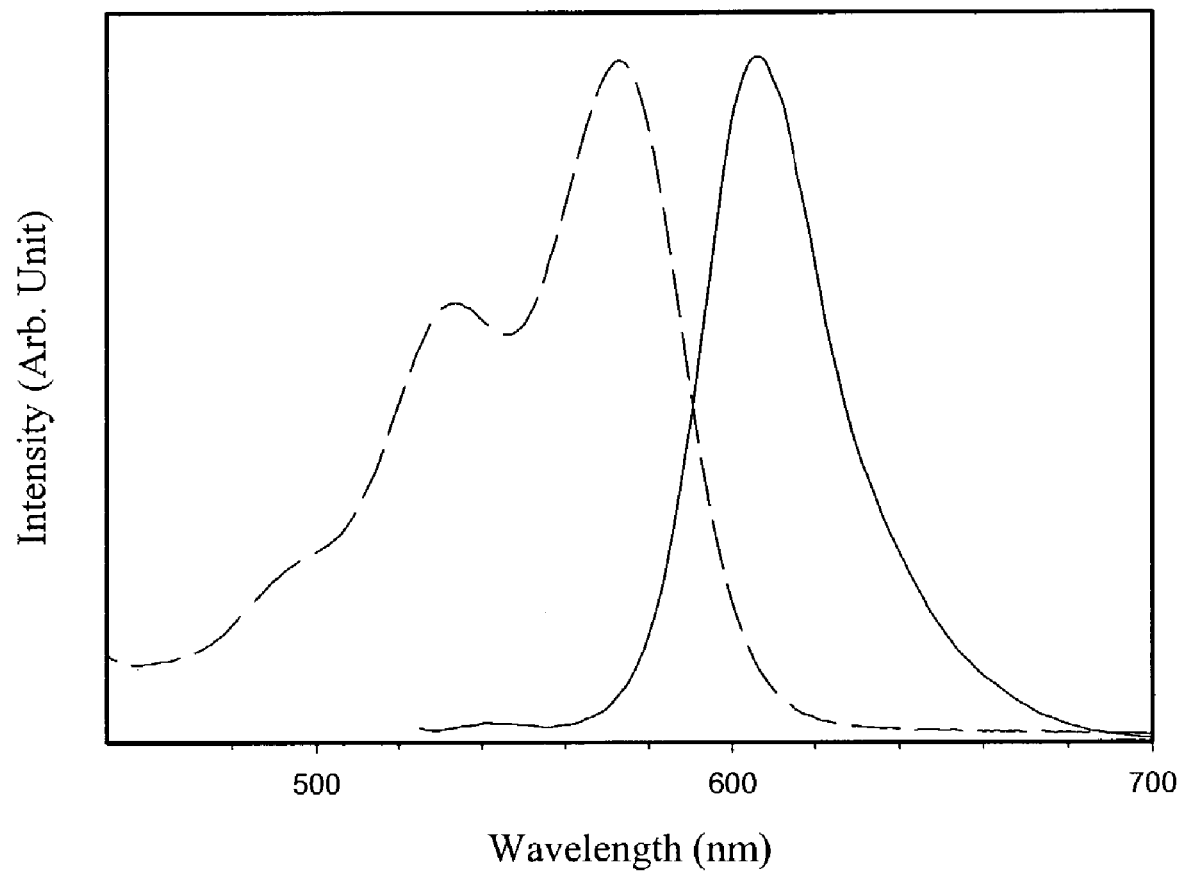
FIG. 2 shows absorption and emission spectra of pAAA in dilute dichloromethane solution.

FIG. 2 shows the absorption (dashed line) and photoluminescence (solid line) spectra of pAAA in dilute solution. The PL peak of pAAA is 608 nm. The width of the PL peak is only 40 nm, and such a narrow emission is very attractive because it shows that high colour purity can be obtained.

Example 4

Manufacture of an Organic EL Device 100 According to FIG. 1

An ITO glass substrate (102 plus 104) was cleaned with detergent and deionized water and dried in an oven for about two hours. It was then treated with UV-ozone for 25 minutes before loading into a deposition chamber. Organic films of hole-transport layer (112), N,N'-bis-(1-naphthyl)-N,N'-diphenylbenzidine (NPB) (700 Angstroms), was deposited using a tantalum boat. Then, a light-emitting layer 120 of doped 1,9-peri-(9'-anthrylene)-10-(9'-anthryl)anthracene (pAAA) in $AlQ_3$ (tris(8-hydroxy-quinolinato)aluminum (III)) (350 Angstroms) was sequentially deposited onto the hole transporting layer 112. The concentration of the dopant compound in AlQ₃ was 2% (in weight). An electron-transport layer 114 of AlQ₃ (350 Angstroms) was then deposited onto the light-emitting layer 120. Finally, a cathode 108 (2000 Angstroms) comprising 10:1 Mg and Ag was deposited on the top of layer 114. The resulting device had the structure ITO/NPB (70 nm)/AlQ₃-2% pAAA (35 nm)/AlQ₃ (35 nm)/Mg:Ag (200 nm).

Figure 3:
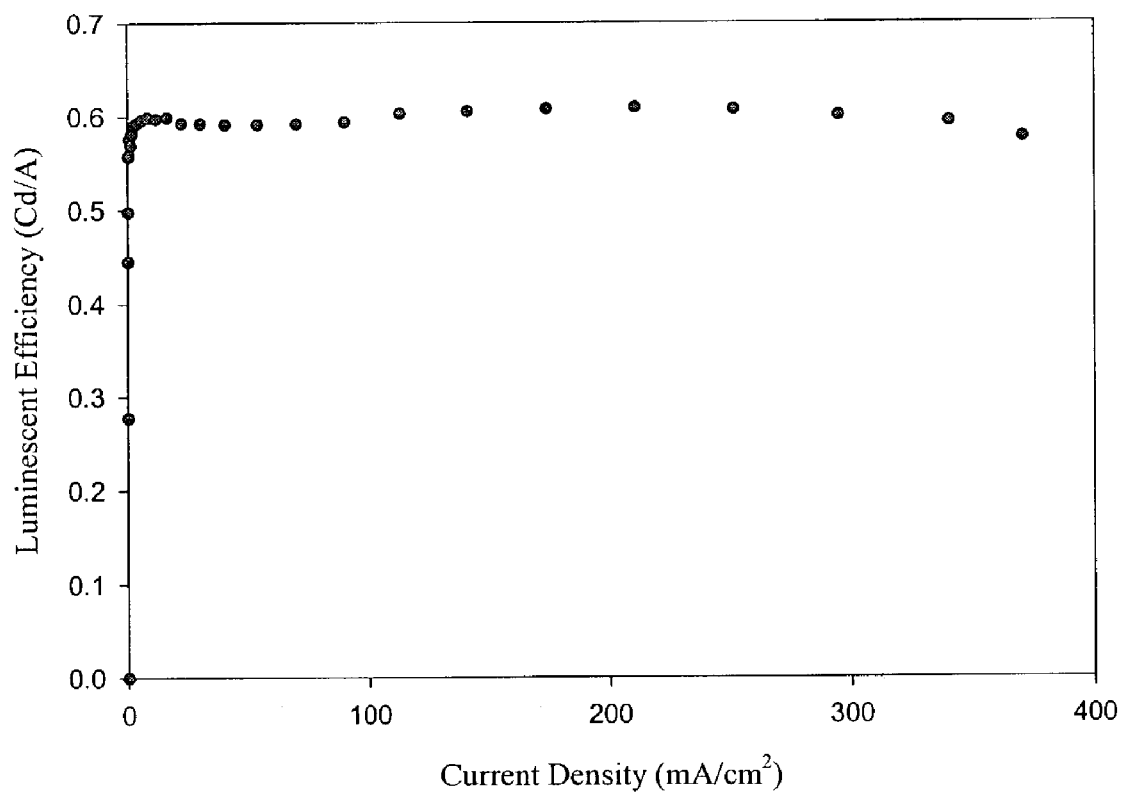
FIG. 3 shows the red organic LED current efficiency characteristics using pAAA as a dopant emitter.

Devices made in accordance with this example, using pAAA dopants, can achieve a current efficiency 0.6 cd $A^{-1}$ with a CIE coordinate x=0.625, y=0.358. The plot of luminance efficiency vs. current density is shown in FIG. 3. The efficiency is almost constant over a large range of current density, with a maximum value of about 0.6 cd $A^{-1}$. The constant efficiency will facilitate the design of driving circuits in OLED displays.

Example 5

Manufacture of an Organic EL Device 100 According to FIG. 1, Wherein the Dopant is Mixed with an Electron Transport Material in a Ratio of 1:200

An ITO glass substrate (102 plus 104) was cleaned with detergent and deionized water and dried in an oven for about two hours. It was then treated with UV-ozone for 25 minutes before loading into a deposition chamber. Organic films of hole-transport layer (112), N,N'-bis-(1-naphthyl)-N,N'-diphenylbenzidine (NPB) (700 Angstroms), were deposited using a tantalum boat. Then, a light-emitting layer 120 of a mixture containing 1,9-peri-(9'-anthrylene)-10-(9'-anthryl) anthracene (pAAA) and AlQ₃ (tris(8-hydroxy-quinolinato) aluminum(III)) in a weight ratio of 1:200 (350 Angstroms) was sequentially deposited onto the hole-transporting layer 112. An electron-transport layer 114 of AlQ₃ (350 Angstroms) was then deposited onto the light-emitting layer 120. Finally, a cathode 108 (2000 Angstroms) comprising 10:1 Mg and Ag was deposited on the top of layer 114.

When tested over the whole injection current, the device exhibited a constant efficiency of around 0.53 Cd/A. The colour of emission was red and peaked at 617 nm with a tail attributing to the excimer of pAAA emission.

The foregoing is offered primarily for the purposes of illustration. It will be readily apparent to those skilled in the art that numerous variations, modifications and substitutions may be made in the materials, procedural steps and conditions described herein without departing from the spirit and scope of the invention.

What is claimed is:

1. A compound of formula [I]:

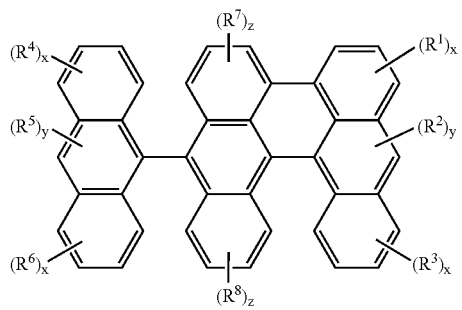

wherein each $R^1$ to $R^8$ is independently selected from the group consisting of halogen atoms, cyano, isocyano, mercapto, amino, carbonyl, carboxy, sulfone, nitro and hydroxy groups, and optionally substituted alkyl other than tert-butyl, alkenyl, alkynyl, haloalkyl, hydroxyalkyl, aryl, alkoxy, aryloxy, alkylamino, arylamino, alkylarylamino, amide, alkylthio, arylthio, alkoxy carbonyl, siloxy, cyclic hydrocarbon or heterocyclic groups;

each x is independently zero, one, two or three;
each y is independently zero or one; and
each z is independently zero, one, two or three.

2. A compound according to claim 1 wherein each $R^1$ to $R^8$ is independently selected from the group consisting of halogen atoms, hydroxy, cyano, isocyano, amino, carbonyl, sulfone and nitro groups, and optionally substituted alkyl other than tert-butyl, alkenyl, allyl, alkoxy, aryl, alkylamino, arylamino, amide, alkoxy and heterocyclic groups.

3. A compound according to claim 1 wherein each x is zero.

4. A compound according to claim 1 wherein each y is zero.

5. A compound according to claim 1 wherein each z is zero.

6. A compound according to claim 1 and having the formula:

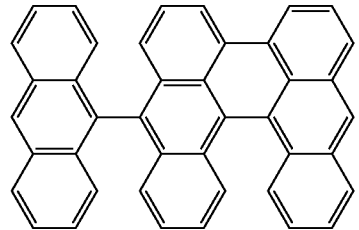

7. An organic electroluminescence device comprising an anode, a cathode, a luminescent layer, at least one hole-transporting layer disposed between the said anode and said luminescent layer, at least one electron-transporting layer disposed between said cathode and said luminescent layer, and a substrate present on either the anode or cathode, wherein the luminescent layer comprises a compound of formula [I]:

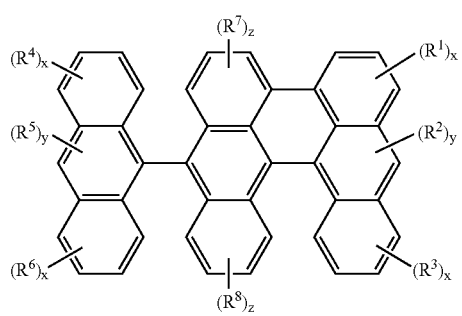

wherein each $R^1$ to $R^8$ is independently selected from the group consisting of halogen atoms, cyano, isocyano, mercapto, amino, carbonyl, carboxy, sulfone, nitro and hydroxy groups, and optionally substituted alkyl, alkenyl, alkynyl, haloalkyl, hydroxyalkyl, aryl, alkoxy, aryloxy, alkylamino, arylamino, alkylarylamino, amide, alkylthio, arylthio, alkoxy carbonyl, siloxy, cyclic hydrocarbon or heterocyclic groups;

each x is independently zero, one, two or three;

each y is independently zero or one; and each z is independently zero, one, two or three.

8. An organic electroluminescence device according to claim 7 wherein the compound of formula [I] is present as a dopant within a host material.

9. An organic electroluminescence device according to claim 8 wherein the host material is selected from the group consisting of tris(8-hydroxy-quinolinato)aluminium (AlQ$_3$), N,N'-bis(1-naphthyl)-N,N'-diphenyl-1,1'-biphenyl-4,4'-diamine (NPB) and a trimer of N-arylbenzimidazoles (TPBI).

10. An organic electroluminescence device according to claim 7 wherein each $R^1$ to $R^8$ is independently selected from the group consisting of halogen atoms, hydroxy, cyano, isocyano, amino, carbonyl, sulfone and nitro groups, and optionally substituted alkyl, alkenyl, allyl, alkoxy, aryl, alkylamino, arylamino, amide, alkoxy carbonyl and heterocyclic groups.

11. An organic electroluminescence device according to claim 7 wherein each x is zero.

12. An organic electroluminescence device according to claim 7 wherein each y is zero.

13. An organic electroluminescence device according to claim 7 wherein each z is zero.

14. A method of using a compound of formula [I] in an electroluminescence device:

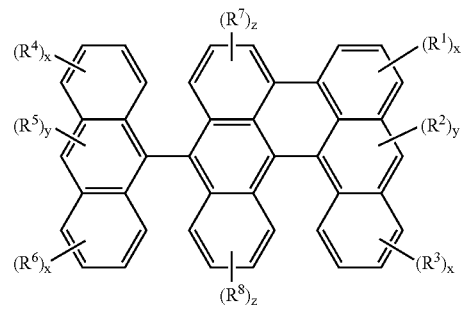

wherein each $R^1$ to $R^8$ is independently selected from the group consisting of halogen atoms, cyano, isocyano, mercapto, amino, carbonyl, carboxy, sulfone, nitro and hydroxy groups, and optionally substituted alkyl, alkenyl, alkynyl, haloalkyl, hydroxyalkyl, aryl, alkoxy, aryloxy, alkylamino, arylamino, alkylarylamino, amide, alkylthio, arylthio, alkoxy carbonyl, siloxy, cyclic hydrocarbon or heterocyclic groups;
each x is independently zero, one, two or three;
each y is independently zero or one; and
each z is independently zero, one, two or three;
the method comprising providing a compound of formula [I], and incorporating said compound as a luminescent material within an electroluminescence device which further comprises an anode, a cathode, a hole-transporting layer and an electron-transporting layer.

15. The method according to claim 14 wherein the compound of formula [I] is present as a dopant within a host material.

* * * * *